US007901907B2

(12) United States Patent
Byrne et al.

(10) Patent No.: US 7,901,907 B2
(45) Date of Patent: Mar. 8, 2011

(54) PROCESS FOR PRODUCTION OF *HELICOBACTER PYLORI* BACTERIOFERRITIN

(75) Inventors: William Byrne, Mount Merrion (IE); Dermot P. Kelleher, Dun Laoghaire (IE); Henry Windle, Dublin (IE); Ross McManus, Dublin (IE)

(73) Assignee: The Provost Fellows and Scholars of the College of the Holy and Undivided Trinity of Queen Elizabeth near Dublin, Dublin (IE)

( * ) Notice: Subject to any disclaimer, the term of this patent is extended or adjusted under 35 U.S.C. 154(b) by 0 days.

(21) Appl. No.: 11/510,509

(22) Filed: Aug. 25, 2006

(65) Prior Publication Data

US 2007/0110765 A1    May 17, 2007

Related U.S. Application Data

(63) Continuation of application No. 11/326,200, filed on Jan. 5, 2006, now abandoned, which is a continuation of application No. 11/112,735, filed on Apr. 22, 2005, now abandoned, which is a continuation of application No. 10/928,353, filed on Aug. 27, 2004, now abandoned, which is a continuation of application No. 10/699,624, filed on Oct. 31, 2003, which is a continuation of application No. 10/342,431, filed on Jan. 13, 2003, now abandoned, which is a continuation of application No. 10/140,758, filed on May 7, 2002, now abandoned, which is a continuation of application No. 09/101,158, filed as application No. PCT/IE97/00001 on Jan. 3, 1997, now abandoned.

(30) Foreign Application Priority Data

Jan. 4, 1996  (IE) .......................................... 960004
Jan. 12, 1996  (IE) .......................................... 960019

(51) Int. Cl.
C12P 21/06    (2006.01)
(52) U.S. Cl. ........................... 435/69.1; 435/71.1; 435/6
(58) Field of Classification Search ........................ None
See application file for complete search history.

(56) References Cited

U.S. PATENT DOCUMENTS

| 4,879,213 A | 11/1989 | Fox et al. ............................ 435/5 |
| 4,882,271 A | 11/1989 | Evans et al. ........................ 435/7 |
| 4,997,823 A * | 3/1991 | Herschler ...................... 514/154 |
| 5,190,961 A | 3/1993 | Hasegawa |
| 5,214,053 A | 5/1993 | Nakazawa |
| 5,262,156 A | 11/1993 | Alemohammad ............... 424/92 |
| 5,292,658 A | 3/1994 | Cormier et al. ........... 435/252.33 |
| 5,306,492 A | 4/1994 | Porro ......................... 424/194.1 |
| 5,354,854 A | 10/1994 | Bourque et al. ............. 536/23.1 |
| 5,403,924 A | 4/1995 | Cover et al. ................. 536/23.1 |
| 5,434,253 A | 7/1995 | Thompson et al. .......... 536/23.2 |
| 5,527,669 A | 6/1996 | Resnick |
| 5,527,678 A | 6/1996 | Blaser et al. ....................... 435/6 |
| 5,538,729 A | 7/1996 | Czinn et al. ................. 424/234.1 |
| 5,541,291 A | 7/1996 | Keene ........................... 530/350 |
| 5,554,372 A | 9/1996 | Hunter |
| 5,567,594 A | 10/1996 | Calenoff ...................... 435/7.32 |
| 5,571,515 A | 11/1996 | Scott et al. ................. 424/208.1 |
| 5,721,349 A | 2/1998 | Cover et al. ................. 536/22.1 |
| 5,723,127 A | 3/1998 | Scott et al. ................. 424/184.1 |
| 5,733,740 A | 3/1998 | Cover et al. ................. 435/7.32 |
| 5,814,455 A | 9/1998 | Pronovost et al. ............ 435/7.1 |
| 5,817,289 A * | 10/1998 | Klaveness et al. .......... 424/1.11 |
| 5,854,221 A | 12/1998 | Cao et al. ........................ 81/434 |
| 5,858,352 A | 1/1999 | Pace et al. .................... 424/93.4 |
| 5,861,518 A | 1/1999 | Dekker |
| 5,866,375 A | 2/1999 | Figura et al. ................. 435/71.3 |
| 5,869,066 A | 2/1999 | Pace et al. ................. 424/282.1 |
| 5,871,749 A | 2/1999 | Doidge et al. .............. 424/234.1 |
| 5,876,943 A | 3/1999 | Cover et al. ....................... 435/6 |
| 5,891,890 A | 4/1999 | Nishino et al. ................ 514/331 |
| 5,895,653 A | 4/1999 | Eibl et al. ................... 424/204.1 |
| 5,897,475 A | 4/1999 | Pace et al. ................. 435/252.1 |
| 5,900,372 A | 5/1999 | Figura et al. ............... 435/252.6 |
| 5,900,410 A | 5/1999 | Hartmann |
| 5,925,667 A | 7/1999 | Nishino et al. ................ 514/428 |
| 5,985,243 A | 11/1999 | Ghiara ........................... 424/9.2 |
| 6,001,880 A | 12/1999 | Nishino et al. ................ 514/617 |
| 6,005,090 A | 12/1999 | Doidge et al. ............... 536/23.5 |
| 6,013,463 A | 1/2000 | Cover et al. ................. 435/7.92 |
| 6,019,982 A | 2/2000 | Clements et al. ........... 424/236.1 |
| 6,054,132 A | 4/2000 | Cover et al. ................. 424/186.1 |
| 6,077,830 A | 6/2000 | Vertesy et al. .................. 514/25 |
| 6,090,611 A | 7/2000 | Covacci et al. ............ 435/252.3 |

(Continued)

FOREIGN PATENT DOCUMENTS

CA    2117490    2/1992

(Continued)

OTHER PUBLICATIONS

Feng et al (Infection and Immunity, 64(1):363-365, 1996).*
Sandbrook (Molecular Cloning A Laboratory Manual, Cold Spring Harbor Press, Ch 17, 1989).*
Harlow et al (Antibodies: A Laboratory Manual, Chapter 5, 1988).*
Campbell, A., Monoclonal Antibody Technology, Elsevier Science Publishers, Ch 1, 1984.*
Evans et al, Gene 153:123-127, Feb. 1995.*
Campbell, (Monoclonal Antibody Technology, Elsevier Science Publishers, 1984, Chapter 1).*
Vogel (Annals of the NY Academy of Sciences 754:153-160, 1995).*
U.S. Appl. No. 09/101,158, filed Jul. 30, 1998, Byrne.
U.S. Appl. No. 10/140,758, filed May 7, 2002, Byrne.
U.S. Appl. No. 10/342,431, filed Jan. 13, 2003, Byrne.
U.S. Appl. No. 10/699,624, filed Oct. 31, 2003, Byrne.
U.S. Appl. No. 10/928,353, filed Aug. 27, 2004, Byrne.

(Continued)

*Primary Examiner* — Patricia A Duffy
(74) *Attorney, Agent, or Firm* — Woodcock Washburn LLP

(57) ABSTRACT

A nucleic acid sequence encoding all or part of an 18-19 kDa *Helicobater pylori* protein is described to which immunoreactivity is detected in *H. pylori* negative individuals. A process for the production of a recombinant form of this protein and its use, particularly as a vaccine to provide immunological protection against *H. pylori* infection are also described.

5 Claims, 1 Drawing Sheet

U.S. PATENT DOCUMENTS

| | | | |
|---|---|---|---|
| 6,124,271 A | 9/2000 | Iversen et al. | 514/44 |
| 6,129,923 A | 10/2000 | Doidge et al. | 424/234.1 |
| 6,153,390 A | 11/2000 | Cover et al. | 435/6 |
| 6,160,119 A | 12/2000 | Senn-Bilfinger | 546/83 |
| 6,231,860 B1 | 5/2001 | Fanget et al. | |
| 6,248,329 B1 * | 6/2001 | Chandrashekar et al. | 424/191.1 |
| 6,265,415 B1 | 7/2001 | Amin et al. | 514/300 |
| 6,534,064 B1 | 3/2003 | O'Hagan | |
| 6,552,047 B2 | 4/2003 | Garvey | |
| 6,559,294 B1 | 5/2003 | Griffais et al. | 536/23.1 |
| 6,649,629 B2 | 11/2003 | Bandarage | |
| 6,761,894 B1 * | 7/2004 | Horwitz | 424/248.1 |
| 6,841,155 B1 | 1/2005 | Del Giudice et al. | |
| 6,902,903 B1 | 6/2005 | Quan | |
| 6,914,131 B1 | 7/2005 | Scarlato et al. | 536/23.1 |
| 7,038,012 B1 | 5/2006 | Grandi | |
| 2001/0010821 A1 | 8/2001 | Kelleher et al. | |
| 2002/0064569 A1 | 5/2002 | Hoffman | |
| 2002/0065296 A1 | 5/2002 | Dumas | |
| 2002/0115078 A1 | 8/2002 | Kleanthous | |
| 2003/0105091 A1 | 6/2003 | Riedl | |
| 2004/0005667 A1 | 1/2004 | Ratti et al. | 435/69.3 |
| 2004/0029129 A1 | 2/2004 | Wang | |
| 2004/0033234 A1 | 2/2004 | Berinstein | |
| 2004/0052799 A1 | 3/2004 | Smith et al. | 424/184.1 |
| 2005/0074450 A1 | 4/2005 | Giuliani et al. | |
| 2005/0191316 A1 | 9/2005 | Fraser et al. | 424/190.1 |
| 2006/0292175 A1 | 12/2006 | Polo et al. | |
| 2007/0104731 A1 | 5/2007 | Kelleher et al. | |
| 2007/0110765 A1 | 5/2007 | Bryne | |
| 2007/0243204 A1 | 10/2007 | Covacci et al. | |
| 2009/0100536 A1 | 4/2009 | Adams | |
| 2009/0103536 A1 | 4/2009 | Basso | |
| 2009/0118268 A1 | 5/2009 | Riedl | |
| 2009/0158452 A1 | 6/2009 | Johnson | |

FOREIGN PATENT DOCUMENTS

| | | |
|---|---|---|
| CA | 2308606 A1 | 5/1999 |
| CA | 2307846 A1 | 6/1999 |
| CA | 2425303 A1 | 5/2002 |
| EP | 0 329 570 A2 | 8/1989 |
| EP | 0 367 644 A1 | 5/1990 |
| EP | 0 372 501 A2 | 6/1990 |
| EP | 0 378 881 A1 | 7/1990 |
| EP | 0 427 347 A1 | 5/1991 |
| EP | 0 471 177 A2 | 2/1992 |
| EP | 0 477 508 A1 | 4/1992 |
| EP | 0 761 231 A1 | 3/1997 |
| EP | 1767214 | 3/2007 |
| FR | 2 669 929 | 6/1992 |
| GB | 2 220 221 A | 1/1990 |
| IN | 183034 | 3/1997 |
| IN | 183035 | 4/1997 |
| IN | 9601063 | 3/2005 |
| IN | 240197 | 4/2010 |
| WO | WO 87/05943 A1 | 10/1987 |
| WO | WO 89/08843 A1 | 9/1989 |
| WO | WO 90/04030 A1 | 4/1990 |
| WO | WO 90/06696 A2 | 6/1990 |
| WO | WO 90/14837 A1 | 12/1990 |
| WO | WO 91/09049 A1 | 6/1991 |
| WO | WO 93/16723 | 9/1993 |
| WO | WO 93/17712 A2 | 9/1993 |
| WO | WO 93/18150 A1 | 9/1993 |
| WO | WO 93/20843 | 10/1993 |
| WO | WO 94/09823 | 5/1994 |
| WO | WO 94/21284 | 9/1994 |
| WO | WO 94/21292 A1 | 9/1994 |
| WO | WO 94/26901 | 11/1994 |
| WO | WO 94/26901 A1 | 11/1994 |
| WO | WO 95/03824 A1 | 2/1995 |
| WO | WO 95/14093 | 5/1995 |
| WO | WO 95/17210 A1 | 6/1995 |
| WO | WO 96/01272 A1 | 1/1996 |
| WO | WO 96/01273 A1 | 1/1996 |
| WO | WO 96/02555 A1 | 2/1996 |
| WO | WO 96/29412 A1 | 9/1996 |
| WO | WO 96/40893 A1 | 12/1996 |
| WO | WO 97/01640 A2 | 1/1997 |
| WO | WO 97/23238 | 7/1997 |
| WO | WO 97/25429 A1 | 7/1997 |
| WO | WO 97/37044 | 10/1997 |
| WO | WO 98/04702 A2 | 2/1998 |
| WO | WO 98/16247 A1 | 4/1998 |
| WO | WO 98/18810 A1 | 5/1998 |
| WO | WO 98/20734 A1 | 5/1998 |
| WO | WO 98/27432 A1 | 6/1998 |
| WO | WO 98/37919 A1 | 9/1998 |
| WO | WO 98/40100 A1 | 9/1998 |
| WO | WO 98/42721 A1 | 10/1998 |
| WO | WO 98/43478 | 10/1998 |
| WO | WO 98/52581 A1 | 11/1998 |
| WO | WO 98/54171 A1 | 12/1998 |
| WO | WO 98/55495 A2 | 12/1998 |
| WO | WO 98/56412 | 12/1998 |
| WO | WO 98/57659 A1 | 12/1998 |
| WO | WO 98/58668 A2 | 12/1998 |
| WO | WO 99/00380 A1 | 1/1999 |
| WO | WO 99/11241 A1 | 3/1999 |
| WO | WO 99/28322 A1 | 6/1999 |
| WO | WO 99/28475 A2 | 6/1999 |
| WO | WO 99/36544 A2 | 7/1999 |
| WO | WO 99/44636 A2 | 9/1999 |
| WO | WO 99/52549 A1 | 10/1999 |
| WO | WO 99/53310 A1 | 10/1999 |
| WO | WO 99/57278 A2 | 11/1999 |
| WO | WO 99/57280 A2 | 11/1999 |
| WO | WO 00/07621 A2 | 2/2000 |
| WO | WO 00/23105 A2 | 4/2000 |
| WO | WO 00/27994 A2 | 5/2000 |
| WO | WO 00/37494 A2 | 6/2000 |
| WO | WO 00/56360 A2 | 9/2000 |
| WO | WO 00/56365 A1 | 9/2000 |
| WO | WO 00/61761 A2 | 10/2000 |
| WO | WO 00/62800 A2 | 10/2000 |
| WO | WO 01/21152 A1 | 3/2001 |
| WO | WO 01/21207 A2 | 3/2001 |
| WO | WO 01/52885 A1 | 7/2001 |
| WO | WO 01/70955 | 9/2001 |
| WO | WO 02/45741 A2 | 6/2002 |
| WO | WO 02/077813 | 10/2002 |

OTHER PUBLICATIONS

"New *H. pylori* Therapy Recommendations", *Scrip*, Oct. 1992, 1760, p. 22.

Afonso, L.C.C., et al., "The adjuvant effect of Interleukin-12 in a vaccine", *Science*, 1994, 263, 235-237.

Ahmad, H., et al., "Conjugated polysaccharide vaccines," Infect. Dis. Clin. North Am., 1999, 13(1), 113-133.

Alexander, J.E., et al., "Amino acid changes affecting the activity of pneumolysin alter the behaviour of pneumococci in pneumonia," *Microbial Pathogenesis*, 1998, 24, 167-174.

Alm et al., "Genomic-sequence comparison of two unrelated isolates of the human gastric pathogen *Helicobacter pylori*," *Nature*, 1999, 397, 176-180 and Erratum.

Andersen, et al., "Immunoglobulin G Antibodies to *Helicobacter pylori* in Patients with Dyspeptic Symptoms Investigated by the Western Immunoblot Technique" *J. Clin Microbiol*, 1992, 30(7), 1743-1751.

Apel, I., et al., "Antibody Response of Patients Against a 120 kDa Surface Protein of *Campylobacter pylori*," *Aentralblat fur Bakterio. Microb. Und Hygiene*, 1988, 268, 271-276.

Apostolopoulos, V., et al., The evolution of DNA vaccines, *Curr Opin. Mol. Ther.*, 2000, 2(4), 441-447.

Austin et al., "Structural Comparison of Urease and a GroEL Analog from *Helicobacter pylori*," *J. Bacteriol.*, 1992, 174(22), 7470-7473.

Ballas, Z. K. et al., "Induction of NK Activity in Murine and Human Cells by CpG Motifs in Oligodeoxynucleotides and Bacterial DNA," *J. Immunol.*, 1996, 157, 1840-1845.

Banerjee, S. et al., "Strategies for developing a *Helicobacter pylori* vaccine," *Current Opinion in Gastroenterology*, 1999, 15, 557-561.

Bukanov, N.O. et al., "Ordered cosmid library and high-resolution physical-genetic map of *Helicobacter pylori* strain NCTC11638," *Molecular Microbiol.*, 1994, 11(3), 509-523.

Burgess, W. H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Biol.*, 1990, 111, 2129-2138.

Buttery, J.P., et al., "Designing meningitis vaccines," *J R Coll Physicians Lond*, 2000, 34(2), 163-168.

Cao, J. et al., "Detection of spiral and coccoid forms of *Helicobacter pylori* using a murine monoclonal antibody," *Clinica Chimica ACTA*, 1997, 267, 183-196.

Chen et al., *Exp. Opin. Ther. Patents*, 2000, 10(8), 1221-1232.

Chu, R.S., et al., "CpG oligodeoxynucleotides act as adjuvants that switch on T helper 1(Th1) immunity," *J. Exp. Med.* 1997, 186(10), 1623-1631.

Clayton, C.L. et al., "Molecular Cloning and Expression of *Campylobacter pylori* Species-Specific Antigens in *Escherichia coli* K-12," *Infect. Immunity*, 1989, 57(2), 623-629.

Clayton, C.L., et al., "Molecular cloning of immunodominant antigen epitopes of *Helicobacter pylori* for development of a specific ELISA to diagnose *H. pylori* infection," "*Helicobacter pylori, Gastritis and Peptic Ulcer*," Malfertheiner, P., et al. (Eds.), Spring-Verlag, Berlin, 1990, 167-171.

Costantino, P., et al., "Development and phase 1 clinical testing of a conjugate vaccine against meningococcus A and C," *Vaccine*, 1992, 10, 691-698.

Costantino, P., et al., "Size fractionation of bacterial capsular polysaccharides for their use in conjugate vaccines," *Vaccine*, 1999, 17, 1251-1263.

Covacci, a. et al., "*Helicobacter pylori* Virulence and Genetic Geography," *Science*, 1999, 248, 1328-1333.

Covacci, A., et al., "Molecular characterization of the 128-kDa immunodominant antigen of *Helicobacter pylori*, associated with cytotoxicity and duodenal ulcer," *Proc. Natl. Acad. Sci. USA*, 1993, 90, 5791-5795.

Covacci, A., et al., "Tyrosine-phosphorylated bacterial proteins: Trojan horses for the host cell," *J. Exp. Med.*, 2000, 191(4), 587-592.

Cover et al., "Characterization of and Human Serologic Response to Proteins in *Helicobacter pylori* Broth Culture Supernatants with Vacuolizing Cytotoxin Activity," *Infect. Immun.*, 1990, 58(3), 603-610.

Cover et al., "Purification and Characterization of the Vacuolating Toxin from *Helicobacter pylori*," *J Biol. Chem.*, 1992, 267(15), 10570-10575.

Cover et al., "Serum Neutralizing Antibody Response to the Vacuolating Cytotoxin of *Helicobacter pylori*," *J. Clin. Invest.*, 1992, 90, 913-918.

Cover,T.L., et al., "Human serologic response to *Campylobacter pylori* cytotoxin-associated proteins," *Gastroenterology*, 1989, 96 (5/2), A101, abstract.

Cowdery, J. S. et al., "Bacterial DNA Induces NK Cells to Produce IFN-γ in Vivo and Increases the Toxicity of Lipopolysaccharides," *J. Immunol*, 1996, 156, 4570-4575.

Crabtree, J.E., et al., "Expression of 120 kilodalton protein and cytotoxicity in *Helicobacter pylori*," *J. Clin. Pathol.*, 1992, 45, 733-734.

Crabtree, J.E., et al., "Mucosal humoral immune response to *Helicobacter pylori*, in patients with duodenitis," *Digestive Diseases & Sciences*, 1991, 36(9), 1266-1273.

Crabtree, J.E., et al., Mucosal IgA recognition of *Helicobacter pylori*, 1991, 338, 332-335.

Crabtree, J.E., et al., "Systemic and mucosal humoral responses to *Helicobacter pylori* in gastric cancer," *Gut.*, 1993, 34, 1339-1343.

Cussac et al., "Expression of *Helicobacter pylori* Urease Genes in *Escherichia coli* Grown under Nitrogen-Limiting Conditions," *J. Bacteriol.*, 1992, 174(8), 2466-2473.

Dale, J.B., "Group a streptococcal vaccines," *Infect. Dis. Clin. North Am.*, 1999, 13(1), 227-243, viii.-ix.

Davis et al., "CpG DNA is a potent enhancer of specific Immunity in Mice immunized with Recombinant Hepatitis B Surface Antigen", *J. Immunol.*, 1998, 160, 870-876.

Davis, H.L., "DNA vaccines for prophylactic or therapeutic immunization against hepatitis B virus," *Mt. Sinai J. Med.*, 1999, 66(2), 84-90.

Del Giudice, G. et al., "The design of vaccines against *Helicobacter pylori* and their development," *Annu. Rev. Immunol.*, 2001, 19, 523-563.

Del Guidice, G., et al., "Molecular basis of vaccination," *Molecular Aspects of Medicine*, 1998, 19, 1-70.

Dick, W.E., Jr., et al., "Glycoconjugates of bacterial carbohydrate antigens," *Contrib Microbiol Immunol, Conjugate Vaccines*, Cruse, J.M.,et al. (Eds.), 1989,10, 48-114, ISBN 3805549326.

Doig, P. et al., "The *Helicobacter pylori* 19.6-kilodalton protein is an iron-containing protein resembling ferritin," *J. Bacteriology*, 1993, 175(2), 557-560.

Donelly, J.J., et al., "Antigen presentation and DNA vaccines," *Am. J. Respir. Crit. Care Med.*, 2000, 162(4 Pt 2), S190-S193.

Donelly, J.J., et al., "DNA vaccines," *Annu. Rev. Immunol.*, 1997, 15, 617-648.

Dooley, C.P., et al., "Prevalence of *Helicobacter pylori* Infection and Histologic Gastritis in Asymptomatic Persons," *New Engl. J. Med.*, 1989, 321, 1562-1566.

Dreesen, D.W., "A global review of rabies vaccines for human use," *Vaccine*, 1997, 15 Suppl, S2-S6.

Drouet, E.B et al., "Characterization of an immunoreactive species-specific 19-kilodalton outer membrane protein from *Helicobacter pylori* by using a monoclonal antibody," *Journal of Clinical Microbiology*, 1991, 29(8), 1620-1624.

Drouet, E.B. et al., "Partial characterization of an external polysaccharide of *Helicobacter pylori* by using an immunoglobulin M monoclonal antibody," *Infection Immunity*, 1993, 61(6), 2732-2736.

Drumm, B., et al., "Intrafamilial Clustering of *Helicobacter pylori* Infection," *New Engl. J. Med.*, 1990, 322(6), 359-363.

Dubensky, T.W., et al., "Delivery systems fro gene-based vaccines," *Mol. Med.*, 2000, 6(9), 723-732.

Dundon, W.G., et al., Virulence factors of *Helicobacter pylori*, *Int. J. Med. Microbiol.*, 2001, 290, 647-658.

Dunn et al., "Identification and Purification of a cpn60 Heat Shock Protein Homolog from *Helicobacter pylori*," *Infect. Immun.*, 1992, 60(5), 1946-1951.

Ellis, R. W., "New technologies for making vaccines," *Vaccines*, Plotkin et al., *W.B. Saunders Company*, 1988, Chapter 29, 568-575.

Ermak et al., "Immunization of Mice with Urease Vaccine affords protection ataint *Helicobacter pylori* infection in the absence of antibodies and is medicated by MHC Class II-restricted responses", *J. Exp. Med.*, 1998, 188, 2277-2288.

Evans et al., "Urease-Associated Heat Shock Protein of *Helicobacter pylori*," *Infect. Immun.*, 1992, 60(5), 2125-2127.

Evans, D.J., et al., "A Sensitive and Specific Serologic Test for Detection of *Campylobacter pylori*Infection," *Gastroenterology*, 1989, 96, 1004-1008.

Evans, Jr, et al., "Identification of four new prokaryotic bacterioferritins, from *Helicobacter pylori, Anabaena variabilis, Bacillus subtilis* and *Treponema pallidum*, by analysis of gene sequences," *Gene*, 1995, 153(1), 123-127.

Evans, Jr. et al., "Characterization of a *Helicobacter pylori* Nuetrophil-Activating Protein," *Infection and Immunity*, 1995, 63(6), 2213-2220.

Fan, X. J. et al., "Gastric T lymphocytes responses to *Helicobacter pylori* patients with *H pylori* colonization," *Gut*, 1994, 35, 1379-1384.

Faulde, M. et al., "Humoral immune response against *Helicobacter pylori* as determined by immunoblot," *Electrophoresis*, 1993, 14, 945-951.

Feldman et al., "Pneumolysin induces the Salient Histologic Features of Pneumococcal infection in the rat lung in Vivo", *Am. J. Respir. Cell Mol. Biol.*, 1991, 5, 416-423.

Ferrero, R.L. et al., "The GroES homolog of *Helicobacter pylori* confers protective immunity against mucosal infection in mice," *Proc. Natl. Acad. Sci*, 1995, 92(4), 6499-6503.

Ferretti, J. J. et al., "Complete genome sequence of an M1 strain of *Streptococcus pyogenes*," *PNAS USA*, 2001, 98, 4658-4663.

Figura, N., et al., "Serum antibodies to the vacuolating toxin produced by *Helicobacter pylori*," *Helicobacter pylori, Gastritis and Peptic Ulcer*, P. Malfertheiner, et al (Eds.), Springer-Verlag, Berlin, 1990, 159-161.

Forman, D., et al., "An international association between *Helicobacter pylori* infection and gastric cancer," *The Lancet*, 1993, 341(8857), 1359-1362.

Forman, D., et al., "Association between infection with *Helicobacter pylori* and risk of gastric cancer: evidence from a prospective investigation," *BMJ*, 1991, 302, 1302-1305.

Forman, D., et al., "Geographic association of *Helicobacter pylori* antibody prevalence and gastric cancer mortality in rural China," *Int. J. Cancer*, 1990, 46, 608-611.

Frazier, B. A. et al., "Paracrystalline Inclusions of a Novel Ferritin Containing Nonheme Iron, Produced by the Human Gastric Pathogen *Helicobacter pylori*: Evidence for a Third Class of Ferritins," *J. Bacteriol*, 1993, 175(4), 966-972.

Fukasawa, L.O., et al., "*Neisseria meningitides* serogroup C polysaccharide and serogroup B outer membrane vesicle conjugate as a bivalent meningococcus vaccine candidate," *Vaccine*, 1999, 17, 2951-2958.

Genisset, C. et al., "A *Helicobacter pylori* vacuolating toxin mutant that fails to oligomerize has a dominant negative phenotype," *Infect Immun.* 2006, 74(3), 1786-1794.

Gerken et al., sequence submitted to EST-STS by Utah Center for Humans Genome Res. University of Utah, 1993, Accession No. L18544.

Gerlich, W.H., et al., "Protective potential of hepatitis B virus antigens other than the S gene protein," *Vaccine*, 1990, 8 Suppl, S63-68 & 79-80.

Gerstenecker, B., et al., "Serodiagnosis of *Helicobacter pylori* Infections with an Enzyme Immunoassay Using the Chromatographically Purified 120 Kilodalton Protein," *Eur. J. Clin. Microbiol. Infect. Dis.*, 1992, 11(7), 595-601.

Ghiara, P. et al., "Therapeutic Intragastric Vaccination against *Helicobacter pylori* in Mice Eradicates an Otherwise Chronic Infection and Confers Protection against Reinfection," *Infection and Immunity*, 1997, 65(12), 4996-5002.

Goddard, A.F., et al., "Review article: urea breath tests for detecting *Helicobacter pylori*," *Aliment. Pharmacol. Ther.*, 1997, 11, 641-649.

Goldblatt, D., "Recent developments in bacterial conjugate vaccines," *J. Med. Microbiol.*, 1998, 47, 563-567.

Goodwin et al., "Transfer of *Campylobacter pylori* and *Campylobacter mustelae* to *Helicobacter* gen. nov. As *Helicobacter pylori* comb. Nov. And *Helicobacter mustelae* comb. Nov., Respectively," *Int. J. Syst. Bacteriol.*, 1989, 39(4), 397-405.

Goto, N., et al., "Histopathological studies of reactions in mice injected with aluminum-adsorbed tetanus toxoid," *Microbiol Immunol.*, 1982, 26(12), 1121-1132.

Goto, N., et al., "Local tissue irritating effects and adjuvant activities of calcium phosphate and aluminium hydroxide with different physical properties," *Vaccine*, 1997, 15(12/13), 1364-1371.

Graham, D.Y., et al., "Seroepidemiology of *Helicobacter pylori* Infection in India: Comparison of Developing and Developed Countries," *Dig. Dis. Sci.*, 1991, 36(8), 1084-1088.

Graham, D.Y., et al., "Epidemiology of *Helicobacter pylori* in an Asymptomatic Population in the United States," *Gastroenterology*, 1991, 100, 1495-1501.

Gustafsson, L. et al., "A Controlled Trial of a Two-Component Acellular, a Five-Component Acellular, and a Whole-Cell Pertussis Vaccine," *N. Engl. J. Med.*, 1996, 334(6), 349-355.

Halpern, M.D., et al., "Bacterial DNA induces murine interferon-γ production by stimulation of interleukin-12 and tumor necrosis factor-α," *Cell. Immunol*, 1996, 167, 72-78.

Hammermeister, I., et al., "Elevated risk of *Helicobacter pylori* infection in submarine crews," *Eur. J. Clin. Microbiol. Infect. Dis.*, 1992, 11(1), 9-14.

Harlow, I., et al. (Ed.), *Antibodies—A Laboratory Manual*, Cold Spring Harbor Laboratory, 1988, Chapter 5, 75-76.

Heap, K., et al., "Immunisation and gastric colonization with *Helicobacter felis*," *Microbial Ecology in Health and Disease, VIth International Workshop on Camplobacter Helicobacter & Related Organisms*, Oct. 7-10, 1991, p. S119.

Hirschl, A. M. et al., "Comparison of ELISA antigen preparations alone or in combination for serodiagnosing *Helicobacter pylori* infections," *J. Clin Pathol.*, 1990, 43, 511-513.

Hirschl, A.M., et al., "Comparison of different antigen preparations in an evaluation of the immune response to *Campylobacter pylori*," *Eur. J. Clin. Microbiol. Infect Dis.*, 1988, 7, 570-575.

Hirschl, A.M., et al., "Serodiagnosis of *Helicobacter pylori* infections: suitablility of various antigen preparations," *Helicobacter pylori, Gastritis and Peptic Ulcer*, Malfertheiner, P., et al. (Eds.), Spring-Verlag, Berlin, 1990, 141-146.

Hofinan, V. et al., "Effect of *Helicbacter pylori* on Polymorphonuclear Leukocyte Migration across Polarized T84 Epithelial Cell Monolayers: Role of Vacuolating Toxin Vaca and cag Pathogenicity Island," *Infection and Immunity*, 2000, 68(9), 5225-5233.

Hsu, H. H. et al., "Prospects for a Hepatitis C Virus Vaccine," *Clin. Liver Dis.*, 1999, 3(4), 901-915.

Huesca, M., et al., "Therapeutics used to alleviate peptic ulcers inhibit *H. pylori* receptors binding in vitro," *Zbl Bakt*, 1993, 280, 244-252.

Ilan, Y., "Technology evaluation: Naked DNA," *Curr. Opin. Mol. Ther.*, 1999, 1, 116-120.

Iwarson, S., "New approaches to hepatitis A and B vaccines," *APMIS*, 1995, 103, 321-326.

Jedrzejas, M. J., "Pneumococcal Virulence Factors: Structure and Function," *Microbiol. Mol. Biol. Rev.*, 2001, 65(2), 187-207.

Ji, X. et al., "Cell Specificity of *Helicobacter pylori* Cytotoxin is Determined by a short Region in the Polymorphic Midregion," *Infect. Immun.*, 2000, 68(6), 3754-3757.

Jiang, S.J., et al., "*Campylobacter*-like organisms in chronic gastritis, peptic ulcer, and gastric carcinoma," *Gastroenterol*, 1987, 22, 553-558.

Joab, I. et al., " Mapping of the gene coding for Epstein-barr virus-determined nuclear antigen EBNA3 and its transient overexpression in a human cell line by using an adenovirus expression vector", *J. Virol.*, Oct. 1987, 61(10), 3340-3344.

Jones et al., "Antibody to the gastric *Campylobacter*-like organism ("*Campylobacter pyloridis*")—Clinical correlations and distribution in the normal population," *Med. Microbiol.*, 1986, 22, 57-62.

Kahn, S. et al., "The major 85-KD surface antigen of the mammalian form of *Trypanosoma cruzi* is encoded by a large heterogeneous family of simultaneously expressed genes," *J. Exp. Med.*, 1990, 172(2), 589-597.

Kalman, S. et al., "Comparative genomes of *Chlamydia pneumoniae* and *C. trachomatis*," *Nature Genetics*, 1999, 21, 385-389.

Karnes, W.E. Jr. et al., "Positive serum antibody and negative tissue staining for *Helicobacter pylori* in subjects with atrophic body gastritis," *Gastroenterology*, 1991, 101, 167-174.

Klinman, D.M., et al., CpG motifs present in bacterial DNA reapidly induce lymphocytes to secrete interleukin 6, interleukin 12, and interferon γ, *Proc. Natl. Acad. Sci. USA*, 1996, 93, 2879-2883.

Krakowka, S. et al., "Establishment of Gastric *Campylobacter pylori* Infection in the Neonatal Gnotobiotic Piglet," *Infection and Immunity*, 1987, 55(11), 2789-2796.

Krieg, A. M., "Immune effects and mechanisms of action of CpG motifs," *Vaccine*, 2000, 19, 618-622.

Krieg, A. M., et al., "CpG motifs in bacterial DNA trigger direct B-cell activation," *Nature*, 1995, 374, 546-549.

Krieg, A. M., et al., "Enhancing vaccines with immune stimulatory CpG DNA," *Curr Opin Mol Ther*, 2001, 3, 15-24.

Kuroda, M., et al., "Whole genome sequencing of meticillin-resistant *Staphylococcus aureus*," *Lancet*, 2001, 357(9264), 1225-1240; see also pp. 1218-1219.

Laemmli, U.K., "Cleavage of structural proteins during the assembly of the head of bacteriophage T4," *Nature*, 1970, 227, 680-685.

Lambert, J. R. et al., "*Campylobacter pyloridis* in diseases of the human upper gastrointestinal tract," *Gastroenterology*, 1986, 90, p. 1509, Abstract.

Lambert, J.R. et al., "*Helicobacter pylori*," *Scand. J. Gastroenterol*, 1995, 208, 33-46.

Lambert, J.R., et al., "Colonization of gnotobiotic piglets with *Campylobacter pyloridis*—an animal model?," *J. of Infectious Disease*, 1987, 155(6), p. 1344.

Lambert, T. et al., "Susceptibility of *Campylobacter pyloridis* to 20 antimicrobial agents," *Antimicrobial Agents and Chemotherapy*, 1986, 30(3), 510-511.

Lazar, E., et al., "Transforming growth factor α: mutation of aspartic acid 47 and leucine 48 results in different biological activities," *Mol of Cell Biol.*, 1988, 8(3), 1247-1252.

Lelwala-Guruge, J. et al., "Immunological properties of the cell surface haemagglutinins (sHAs) of *Helicobacter pylori* strain NCTC 11637," *FEMS Immunology and Medical Microbiol*, 1995, 11(1), 73-77.

Leunk,R.D., "Production of a Cytotoxin by *Helicobacter pylori*," *Rev. Infect. Dis.*, 1991, 13(Suppl. 8), S686-S689.

Leying, H., et al., "Cloning and genetic characterization of a *Helicobacter pylori* flagellin gene," *Mol. Microbiol.*, 1992, 6(19), 2863-2874.

Lindberg, A. A., "Glycoprotein conjugate vaccines," *Vaccine*, 1999, 17 Suppl 2, S28-36.

Lipford, G.B., et al., "CpG-containing synthetic oligonucleotides promote B and cytotoxic T cell responses to protein antigen: a new class of vaccine adjuvants," *Eur. J. Immunol.*, 1997, 27, 2340-2344.

Lischwe, M.A. et al., "A New Method for Partial Peptide Mapping using *N*-chlorosuccinimide/urea and peptide silver staining in sodium dodecyl sulfate-polyacrylamide geis,", *Analytical Biochem*, 1982, 127, 453-457.

Malfertheiner, P. et al., "Rationale for eradication of *Helicobacter pylori* infection in duodenal ulcer disease," *Clinical Therapeutics*, 1993, 15(Suppl B), 37-48.

Malfertheiner P. et al. "Phase I safety and immunogenicity of a three-component *H. pylori* vaccine." Gastroenterology, vol. 122, No. 4 Suppl. 1, Apr. 2002, p. A.585, No. W1195, XP009001958 Digestive Disease Week and the 103rd Annual Meeting of the American Gastroenterological Association;San Francisco, CA, USA; May 19-22, 2002.

Manetti, R., et al., "Detoxification of the *Helicobacter pylori* Cytotoxin," *Infect. Immun.*, 1997, 65(11), 4615-4619.

Manetti, R. et al., "*Helicobacter pylori* Cytotoxin: Importance of Native Conformation for Induction of Neturalizing Antibodies," *Infection and Immunity*, 1995, 63(11), 4476-4480.

Marchetti et al., "Development of a mouse model of *Helicobacter pylori* infection that mimics human disease", *Science*, 1995, 267, 1655-1658.

Marchetti, M. et al., "Protection against *Helicobacter pylori* infection in mice by intragastric vaccination with *H. pylori* antigens is achieved using a non-toxic mutant of *E. coli* heat-labile enterotoxin (LT) as adjuvant" *Vaccine*, 1998, 16, 33-37.

Markwell, M.A.K., et al, "A modification of the lowry procedure to simplify protein determination in membrane and lipoprotein samples," *Analytical Biochemistry*, 1978, 87, 206-210.

Marshall, B.J., et al., "Attempt to fulfil Koch's postulates for *Pyloric campylobacter*," *Med. J. of Australia*, 1985, 142, 436-439.

Marshall, B.J., et al., "Unidentified curved bacilli in the stomach of patients with gastritis and peptic ulceration," *The Lancet*, 1984, 1311-1314.

Matsudaira, P.T., "A Pratical Guide to Protein Purification for . . . ", *Academic Press*, San Diego, 1989, Table of Contents, v -viii and Contributors p. ix.

McClain, M. S. et al., "Essential Role of a GXXXG Motif for Membrane Channel Formation by *Helicobacter pylori* Vacuolating Toxin," *J. Biol. Chem.*, 2003, 278(14), 12101-12108.

McGuinnes, B. et al., "Deduced Amino Acid Sequences of Class 1 Protein (PorA) from Three Strains of *Neisseria meningitidis*," *J. Exp. Med.*, 1990, 171,1871-1882.

McMichael, J.C., "Vaccines for *Moraxella catarrhalis*," *Vaccine*, 2000, 19 Suppl 1, S101-S107.

Messina, J. P. et al., "Stimulation of in vitro murine lymphocyte proliferation by bacterial DNA," *J. Immunol.*, 1991, 147, 1759-1764.

Mitchell et al., "Complement Activation and antibody binding to Pneumolysin via a region of the toxin homologous to a human acute-phase protein", *Mol. Microbiol.*, 1991, 5(8), 1883-1888.

Mitchell, H. M. et al., "Antigen Recognition during Progression from Acute to Chronic Infection with a cagA-Positive Strain of *Helicobacter pylori*," *Infection and Immunity*, 1996, 64(4), 1166-1172.

*MMWR Morb. Mortal. Wkly Rep.*, "Notice to readers availability of new rabies vaccine for human use", 1998, 47(1), pp. 12, 19, 20.

Moldoveanu, Z., et al., "CpG DNA, a novel immune enhancer for systemic and mucosal immunization with influenza virus," *Vaccine*, 1988, 16, 1216-1224.

Moran, A.P. et al., "Cell surface characteristics of *Helicobacter pylori*," *FEMS Immunology Medical Microbiol*, 1995, 10, 271-280.

Morris, A., et al., "Ingestion of *Campylobacter pyloridis* causes gastritis and raised fasting gastric pH," *Am. J. of Gastroenterology*, 1987, 82(3), 192-199.

Morris, A., et al., "Seroepidemiology of *Campylobacter pyloridis*," *N.Z. Med. J.*, 1986, 99(809), 657-659.

Mukhopadhyay, A. K. et al., "Distinctiveness of Genotypes of *Helicobacter pylori* in Calcutta, India," *J. Bacteriol.*, 2000, 182(11), 3219-3227.

Murakami, H. et al., "A genetically engineered P450 monooxygenase: construction of the functional fused enzyme between rat cytochrome P450c and NADPH-cytochrome P450 reductase", *DNA*, 1987, 6(3), 189-197.

Nakajima, H. et al., "A Cytoskeleton-related Gene, USO1, Is Required for Intracellular Protein Transport in *Saccharomyces cerevisae*," *J. Cell. Biol.*, 1991, 113(2), 245-260.

Nedrud, J. G., "Animal models for gastric *Helicobacter* immunology and vaccine studies," *FEMS Immunology and Medical Microbiology*, 1991, 24, 243-250.

Newell, D.G., et al., "Identification of the outer membrane proteins of *Campylobacter pyloridis* and antigenic cross-reactivity between *C. pyloridis* and *C. jejuni*," *J. General Microbiol*, 1987, 133, 163-170.

Nilsson, et al., "Immunoblot Assay for Serodiagnosis of *Helicobacter pylori* Infections," *J. Clin. Microbiol*, 1997, 35(2), 427-432.

Nomura, A., et al., "*Helicobacter pylori* infection and gastric carcinoma among Japanese Americans in Hawaii," *New England J of Medicine*, 1991, 1132-1136.

O'Conner, H.J., "Eradication of *Helicobacter pylori*: therapies and clinical implications," *Postgrad Med. Journal*, 1992, 68, 549-557.

O'Toole, P.W., et al., "Isolation and biochemical and molecular analyses of a species-specific protein antigen from the gastric pathogen *Helicobacter pylori*," *J. of Bacteriology*, 1991, 173(2), 505-513.

Oderda, G. et al., "Serologic IgG recognition of *Helicobacter pylori* cytotoxin-associated protein, peptic ulcer and gastroduodenal pathology in childhood," *European Journal of Gastroenterology & Hepatology*, 1993, 5, 695-699.

Orkin, S.H., et al. (Co-Chairs), *Report and Recommendations of the Panel to Assess the NIH Investment in Research on Gene Therapy*, Dec. 7, 1995, 41 pages.

Palker et al., "Type-specific neutralization of the human immunodeficiency virus with antibodies to *env*-encoded synthetic peptides," *PNAS*, 1988, 85, 1932-1936.

Parsonnet, J., et al., "*Helicobacter pylori* infection and the risk of gastric carcinoma," *N. Engl. J. Med.*, 1991, 325(16), 1127-1131.

Pei, Z. et al., "Identification, Purification, and Characterization of Major Antigenic Proteins of *Campylobacter jejuni*," *J. Biol. Chem.*, 1991, 266(25), 16363-16369.

Perez-Perez et al., "Characteristics of *Helicobacter pylori* Variants Selected for Urease Deficiency," *Infect. Immun.*, 1992, 60(9), 3658-3663.

Peterson, et al., "Structure and functional properties of human general transcription factor IIE," *Nature*, 1991, 354, 369-373.

Pizza, M., et al., "Identification of Vaccine Candidates Against Serogroup B Meningococcus by Whole-Genome Sequencing," *Science*, 2000, 287, 1816-1820.

Pizza, M., et al., "Probing the structure-activity relationship of *Escherichia coli* LT-A by site-directed mutagenesis", *Mol. Microbiol.*, 1994, 14(1), 51-60.

Powell & Newman, *Vaccine Design: The Subunit & Adjuvant Approach*, 1995, Chapter 10 (ISBN: 030644867X).

Radin, M. J. et al., "*Helicobacter pylori* Gastric Infection in Gnotobiotic Beagle Dogs," *Infection and Immunity*, Aug. 1990, 58(8), 2606-2612.

Ramsay, M..E., et al., "Efficacy of meningococcal serogroup C conjugate vaccine in teenagers and toddlers in England," *Lancet*, 2001, 357(9251), 195-196.

Rappuoli, R., et al., "Development of a vaccine against *Helicobacter pylori*: a short overview," *Eur. J. of Gastroenterology & Hepatology*, 1993, 5(Suppl. 2), S76-S78.

Rappuoli, R., et al., "Towards third-generation whooping cough vaccines," *TIBTECH*, 1991, 9, 232-238.

Rauws, E.A.J., et al., "Cure of duodenal ulcer associated with eradication of *Helicobacter pylori*," *Lancet*, 1990, 335, 1233-1235.

Read, T.D., et al., "Genome sequences of *Chlamydia trachomatis* MoPn and *Chlamydia pneumoniae*," *Nucleic Acids Res.*, 2000, 28(6), 1397-406.

Rettenmier, C.W. et al., "Expression of the human *c-fms* proto-oncogene product (colony-stimulating factor-1 receptor) on peripheral blood mononuclear cells and choriocarcinoma cell lines", *J. Clin. Invest.*, June 1986, 77, 1740-1746.

Reyrat, J-M., et al., "Towards deciphering the *Helicobacter pylori* cytotoxin," *Mol. Microbiol.*, 1999, 34(2), 197-204.

Reyrat, J-M. et al., "3D Imaging of the 58 kDa cell Binding Subunit of the *Helicobacter pylori* Cytotoxin," *J. Mol. Biol.*, 1999, 290, 459-470.

Robinson, H.L., "DNA vaccines for viral infections: basic studies and applications," *Adv. Virus Res.*, 2000, 55, 1-74.

Robinson, H.L., et al., "DNA vaccines," *Seminars in Immunology*, 1997, 9, 271-283.

Roman, M., et al., "Immunostimulatory DNA sequences function as T helper-1-promoting adjuvants," *Nat. Med.*, 1997, 3(8), 849-854.

Rosenqvist, E., et al., "Effect of aluminum hydroxide and meningococcal serogroup C capsular polysaccharide on the immunogenicity and reactogenicity of a Group B *Neisseria meningitides* outer membrane vesicle vaccine," *Dev. Biol. Stand.*, 1998, 92, 323-333.

Ross, B. C. et al., "Identification of vaccine candidate antigens from a genomic anlysis of *Porphyromonas gingivalis*," *Vaccine*, 2001, 19, 4135-4142.

Ross, J. S. et al., "Role of Aluminum Sensitivity in Delayed Persistent Immunization Reactions," *J. Clin. Pathol.*, 1991, 44, 876-877.

Rossi et al., "Immunohistochemical study of lymphocyte populations infiltrating the gastric mucosa of beagle dogs experimentally infected with *Helicobacter pylori*," *Infect. Immun.*, 2000, 68(8), 4769-4772.

Rossi, G. et al., A Conventional Beagle Dog Model for Acute and Chronic Infection with *Helicobacter pylori*, *Infect. Immun.*, 1999, 67(6), 3112-3120.

Rubin, L.G., "Pneumococcal vaccine," *Pediatr. Clin. North Am.*, 2000, 47(2), 269-285.

Sarno, M.J., et al., "Clinical immunogenicity of measles, mumps and rubella vaccine delivered by the Injex jet injector: comparison with standard syringe injection," *Pediatr. Infect. Dis. J.*, 2000, 19, 839-842.

Satin, B. et al., "The Neutrophil-activating Protein (HP-NAP) of *Helicobacter pylori* Is a Protective Antigen and a Major Virulence Factor," *J. Exp. Med.*, 2000, 191(9), 1467-1476.

Savarino, V. et al., "The 13C urea breath test in the diagnosis of *Helicobacter pylori* infection," *Gut*, 1999, 45 Suppl. 1, 118-122.

Schmitt, W. et al., "Genetic analysis of the *Helicobacter pylori* vacuolating cytotoxin: structural similarities with the IgA protease type of exported protein," *Mol. Microbiol.*, 1994, 12(2), 307-319.

Schuchat, A., "Group B streptococcus," *Lancet*, 1999, 353(9146), 51-56.

Scott-Taylor & Dalgleish, "DNA Vaccines," *Expert Opin. Investig. Drugs*, 2000, 9, 471-480.

Shirai, M. et al., "Comparison of Outer Membrane Protein Genes omp and pmp in the Whole Genome Sequences of *Chlamydia pneumoniae* Isolates from Japan and the United States," *J. Infect. Dis.*, 2000, 181(Suppl 3), S524-S527.

Sibold, L., et al., "Cloning and expression in *Escherichia coli* of the TL-DNA gene 4 of *Agrobacterium turnefaciens* under the control of the $P_R$ promoter of bacteriophage λ," *Biochimie*, 1984, 66, 547-556.

Stacey, K. J. et al., "Macrophages Ingest and are Activated by Bacterial DNA," *J. Immunol.*, 1996, 157, 2116-2122.

Stunnenberg, H. G. et al., "High expression of functional adenovirus DNA polymerase and precursor terminal protein using recombinant vaccinia virus," *Nucleic Acids Research*, 1988, 16(6), 2431-2444.

Sutter, R.W., et al., "Poliovirus Vaccines: Progress toward global poliomyelitis eradication and changing routine immunization recommendations in the United States," *Pediatr. Clin. North Am.*, 2000, 47(2), 287-308.

Taylor, D.N., et al., "The epidemiology of *Helicobacter pylori* infection," *Epidemiology Reviews*, 1991, 13, 42-59.

Telford, J. L. et al., "Gene Structure of the *Helicobacter pylori* Cytotoxin and Evidence of its Key Role in Gastric Disease," *J. Exp. Med.*, 19914, 179, 1653-1658.

Telford, J.L., et al., "Immunobiology of *Helicobacter pylori* infection," *Curr. Opin. Immunol.*, 1997, 9, 498-503.

Telford, J.L., et al., "Unravelling the pathogenic role of *Helicobacter pylori* in peptic ulcer: potential new therapies and vaccines," *TIBTECH*, 1994, 12, 420-426.

Tettelin et al., "Complete Genome Sequence of *Neisseria meningitides* Serogroup B Strain MC58," *Science*, 2000, 287, 1809-1815.

Thomas, J.E., et al., "Isolation of *Helicobacter pylori* from human faeces," *Lancet*, 1992, 340, 1194-1195.

Tomb, J.-F., et al., "The complete genome sequence of the gastric pathogen *Helicobacter pylori*," *Nature*, 1997, 388(7), 539-547 (plus errata).

Tonello, F. et al., "The *Helicobacter pylori* neutrophil-activating protein is an iron-binding protein with dodecameric structure," *Mol. Microbiol.*, 1999, 34, 238-246.

Trevino, L.B. et al., "Expression of *Mycoplasma pneumoniae* antigens in *Escherichia coli*", *Infection and Immunity*, 1986, 53(1), 129-134.

Tummuru, M., et al., "Molecular cloning of a unique antigen of *Helicobacter pylori*," Abstracts of the 91$^{st}$ General Meeting of the American Society for Microbiology, Dallas, TX, May 5-9, 1991 (abstract B-127).

Tummuru, M.K.R., et al., "Cloning and Expression of a High-Molecular-Mass Major Antigen of *Helicobacter pylori*: Evidence of Linkage to Cytotoxin Production", *Infection and Immunity*, 1993, 61(5), 1799-1809.

Vaira, D., et al., "Accurate diagnosis of *Helicobacter pylori*: stool tests," *Gastroenterol. Clin. North Am.*, 2000, 29(4), 917-923.

Vaira, et al., "Peptide ulcer disease and *Helicobacter pylori* infection,", *Current Opinion in Gastroenterology*, 1994, 10(1), 98-104.

Vinion-Dubiel, A. D. et al., "A Dominant Negative Mutant of *Helicobacter pylori* Vacuolating Toxin (VacA) Inhibits VacA-induced Cell Vacuolation," *J. Biol. Chem.*, 1999, 37736-37742.

Von Wulffen, H. et al., "Immunoblot analysis of immune response to *Campylobacter pylori* and its clinical associations," *J. Clin Pathol.*, 1988, 41, 653-659.

Warren et al., "Unidentified Curved Bacilli on Gastric Epithelium in Active Chronic Gastritis," *Lancet*, 1983, 1273-1275.

Watson, W., "Pneumococcal conjugate vaccines," *Pediatr. Infect. Dis. J.*, 2000, 19, 331-332.

Weiner, G.J., et al., "Immunostimulatory oligodeoxynucleotides containing the CpG motif are effective as immune adjuvants in tumor antigen immunization," *Proc. Natl. Acad. Sci. USA*, 1997, 94, 10833-10837.

Yamamoto, S., et al., "In vitro augmentation of natural killer cell activity and production of interferon-α/β and -γ with deoxyribonucleic acid fraction from *Mycobacterium bovis* BCG," *Jpn. J. Cancer Res.*, 1988, 79, 866-873.

Yi, A.-K., et al., "CpG DNA rescue of murine B lymphoma cells from Anti-IgM-induced growth arrest and programmed cell death is associated with increased expression of c-myc and bcl-$X_L^{1,2}$," *J. Immunol.*, 1996, 157, 4918-4925.

Yi, A.-K., et al., "CpG motifs in bacterial DNA activate leukocytes through the pH-dependent generation of reactive oxygen species," *J. Immunol.*, 1998, 160, 4755-4761.

Yi, A-K. et al., "CpG Oligodeoxyribonucleotides Rescue Mature Spleen B Cells from Spontaneous Apoptosis and Promote Cell Cycle Entry," *J. Immunol.*, 1998, 160, 5898-5906.

Yi, A-K. et al., "Rapid Immune Activation by CpG Motifs in Bacterial DNA," *J. Immunol.*, 1996, 157, 5394-5402.

Zimmerman, R.K., et al., "Poliovirus vaccine options," *Am. Fam. Physician*, 1999, 59(1), 113-118 and 125-126, downloaded from the Internet on Apr. 18, 2006 (9 pages).

Dunkley et al., Microb. Ecol. Health Dis., 1991, 4(spec. issue), S148.

Stein, M. et al., "c-Src/Lyn kinases activate *Helicobacter pylori* CagA through tyrosone phosphorylation of the EPIYA motifs," Molecular Microbiology, 2002, 43(4), 971-980.

Xiang, Z. et al., "Detection in a Enzyme Immunoassay of an Immune Response to a Recombinant of the 128 Kilodalton Protein (CagA) of *Helicobacter pylori*," Eur. J. Clin. Microbiol. Infect. Dis., Oct. 1993, 739-745.

Censini et al., "cag, a pathogenicity island of *Helicobacter pylori*, encodes type I-specific and disease-associated virulence factors", Proc Natl Acad Sci U S A., Dec. 10, 1996, 93(25), 14648-14653.

Copass et al., "Introduction of unmarked mutations in the *Helicobacter pylori* vacA gene with a sucrose sensitivity marker", Infect Immun., May 1997, 65(5), 1949-1952.

Covacci et al., "Tyrosine-phosphorylated bacterial proteins, Trojan horses for the host cell", J Exp Med., Feb. 21, 2000, 191(4), 587-592.

Crabtree et al., "*Helicobacter pylori* induced interleukin-8 expression in gastric epithelial cells is associated with CagA positive phenotype", J Clin Pathol., Jan. 1995, 48(1), 41-45.

De Bernard et al., "*Helicobacter pylori* toxin VacA induces vacuole formation by acting in the cell cytosol", Mol Microbiol., Nov. 1997, 26(4), 665-674.

De Bernard et al., "Identification of the *Helicobacter pylori* VacA toxin domain active in the cell cytosol", Infect Immun., Dec. 1998, 66(12), 6014-6016.

De Bernard et al., "Low pH activates the vacuolating toxin of *Helicobacter pylori*, which becomes acid and pepsin resistant", J Biol Chem., Oct. 13, 1995, 270(41), 23937-23940.

D'Elios et al., "Different cytokine profile and antigen-specificity repertoire in *Helicobacter pylori*-specific T cell clones from the antrum of chronic gastritis patients with or without peptic ulcer", Eur J Immunol., Jul. 1997, 27(7), 1751-1755.

D'Elios et al., "Impaired T-cell regulation of B-cell growth in *Helicobacter pylori*—related gastric low-grade MALT lymphoma", Gastroenterology., Nov. 1999, 117(5), 1105-1112.

D'Elios et al., "T helper 1 effector cells specific for *Helicobacter pylori* in the gastric antrum of patients with peptic ulcer disease", J Immunol., Jan. 15, 1997, 158(2), 962-967.

Di Tommaso et al., "*Helicobacter pylori*-specific CD4+ T-cell clones from peripheral blood and gastric biopsies", Infect Immun., Mar. 1995, 63(3), 1102-1106.

Ghiara et al., "Role of the *Helicobacter pylori* virulence factors vacuolating cytotoxin, CagA, and urease in a mouse model of disease", Infect Immun., Oct. 1995, 63(10), 4154-4160.

Ilver et al., "*Helicobacter pylori* adhesin binding fucosylated histo-blood group antigens revealed by retagging", Science., Jan. 16, 1998, 279(5349), 373-377.

Lupetti et al., "Oligomeric and subunit structure of the *Helicobacter pylori* vacuolating cytotoxin", J Cell Biol., May 1996, 133(4), 801-807.

Luzzi et al., "Detection of a vacuolating cytotoxin in stools from children with diarrhea", Clin Infect Dis., Jul. 1996, 23(1), 101-106.

Macchia et al., "The Hsp60 protein of *Helicobacter pylori*, structure and immune response in patients with gastroduodenal diseases", Mol Microbiol., Aug. 1993, 9(3), 645-652.

Molinari et al., "Selective inhibition of Ii-dependent antigen presentation by *Helicobacter pylori* toxin VacA", J Exp Med., Jan. 5, 1998, 187(1), 135-140.

Molinari et al., "Vacuoles induced by *Helicobacter pylori* toxin contain both late endosomal and lysosomal markers", J Biol Chem., Oct. 3, 1997, 272(40), 25339-25344.

O'Toole et al., "The putative neuraminyllactose-binding hemagglutinin HpaA of *Helicobacter pylori* CCUG 17874 is a lipoprotein", J Bacteriol, Nov. 1995, 177(21), 6049-6057.

Pagliaccia et al., "The m2 form of the *Helicobacter pylori* cytotoxin has cell type-specific vacuolating activity", Proc Natl Acad Sci U S A., Aug. 18, 1998, 95(17), 10212-10217.

Papini et al., "Cellular vacuoles induced by *Helicobacter pylori* originate from late endosomal compartments", Proc Natl Acad Sci U S A., Oct. 11, 1994, 91(21), 9720-9724.

Papini et al., "Selective increase of the permeability of polarized epithelial cell monolayers by *Helicobacter pylori* vacuolating toxin", J Clin Invest., Aug. 15, 1998, 102(4), 813-820.

Papini et al., "The small GTP binding protein rab7 is essential for cellular vacuolation induced by *Helicobacter pylori* cytotoxin", EMBO J., Jan. 2, 1997, 16(1), 15-24.

Rossi et al., "A conventional beagle dog model for acute and chronic infection with *Helicobacter pylori*", Infect Immun., Jun. 1999, 67(6), 3112-3120.

Segal et al., "Induction of host signal transduction pathways by *Helicobacter pylori*", Proc Natl Acad Sci U S A., Jul. 8, 1997, 94(14), 7595-7599.

Stein et al., "Tyrosine phosphorylation of the *Helicobacter pylori* CagA antigen after cag-driven host cell translocation", Proc Natl Acad Sci U S A., Feb. 1, 2000, 97(3), 1263-1268.

Xiang et al., "Analysis of expression of CagA and VacA virulence factors in 43 strains of *Helicobacter pylori* reveals that clinical isolates can be divided into two major types and that CagA is not necessary for expression of the vacuolating cytotoxin", Infect Immun., Jan. 1995, 63(1), 94-98.

Xiang et al., "*Helicobacter pylori*, host responses in peptic ulceration", Lancet., Apr. 3, 1993, 341(8849), 900-901.

Barton, S.G. R. et al., "Circulating IGA antibodies to the 60KDA heat shock protein family are raised in patients with *Helicobacter pylori*-related gastric atrophy," Gut, 1995, 37(suppl 1) p. A80, abstract 319.

Beales, I., et al., "Antibodies to CAG a protein in patients with *H. pylori* infection and atrophic gastritis," Gut, 1995, 37, (suppl. 1), p. A37, abstract 145.

Bell, B.P., "Hepatitis a vaccine," Pediatr. Infect. Dis. J., 2000, 19, 1187-1188.

Bjune, G., et al., "Effect of outer membrane vesicle vaccine against group B meningococcal disease in Norway," Lancet, 1991, 338(8775), 1093-1096.

Blaser, M., "*H. pylori* associated disease involves host and bacterial factors," HP World-Wide, Feb. 1992, 1-8.

Blaser, M.J., "*Helicobacter pylori*: Its Role in Disease," Clin. Infect. Dis., 1992, 15, 386-391.

Blaser, M.J., "Gastric *Campylobacter*-like Organisms, Gastritis, and Peptic Ulcer Disease," Gastroenterology, 1987, 93, 371-383.

Blaser, M.J., "*Helicobacter pylori* and the pathogenesis of gastroduodenal inflammation," J. of Infectious Diseases, 1990, 161, 626-633.

Blaser, M.J., "Hypotheses on the pathogenesis and natural history of *Helicobacter pylori*-induced inflammation," Gastroenterology, 1992, 102, 720-727.

Brown, W.E., et al., "Quantitation and characterization of the trifluoroacetonyl derivative of cysteine: a useful NMR probe," Analytical Biochem., 1978, 87, 211-222.

Browne, M. W., "European Scientists Win Physics and Chemistry Nobel Prizes," New York Times (National Edition), Oct. 17, 1991, p. A16.

Buck, G.E. et al., "Relation of *Campylobacter pyloridis* to gastritis and peptic ulcer," J. Infectious Diseases, 1986, 153(4), 664-669.

Altman, "Stomach Cancer is Linked to Persistent Infection With a Common Bacterium", New York Times (national edition), Oct. 17, 1991, original print p. A16, electronic version 2 pages.

Boslego et al., "Gonorrhea Vaccines," Vaccines and Immunotherapy, Chapter 17, No Month Available, 1991, pp. 211-223.

Evans et al., "Cloning, Nucleotide Sequence, and Expression of a Gene Encoding an Adhesin Subunit Protein of Helicobacter pylori," Journal of Bacteriology, Feb. 1993, vol. 175, No. 3, pp. 674-683.

Fomb et al., "The complete genome sequence of the gastric pathogen *Helicobacter pylori*", Nature, Aug. 7, 1997, 388(6644), 539-547.

Yokota et al., "Low antigenicity of the polysaccharide region of *Helicobacter pylori* lipopolysaccharides derived from tumors of patients with gastric cancer", Infection and Immunity, Sep. 1997, 65(9), 3509-3512.

U.S. Appl. No. 08/775,765: Office Action dated May 7, 2002, 12 pages.

U.S. Appl. No. 08/775,765: Office Action dated Jun. 28, 2000, 20 pages.

Dietrich, 1999 (No further citation information available. Comments provided in Information Disclosure Statement transmittal).

Lee et al., "Oral immunization with recombinant *Helicobacter pylori* urease induces secretory IgA antibodies and protects mice from challenge with *Helicobacter felis*", J Infect Dis., Jul. 1995, 172(1), 161-172.

Nakata et al., "Serum antibody against *Helicobacter pylori* assayed by a new capture ELISA", J Gastroenterol., Jun. 1995, 30(3), 295-300.

Agarwal, "*Helicobacter Pylori* Vaccine: From Past to Present", Mayo Clin Proc, Feb. 2008, 83(2),169-175.

Bixler et al., "Synthetic Vaccines", (no month available) 1987, 1, 39-71.

Bowie, "Deciphering the Message in Protein Sequences: Tolerance to Amino Acids", Science, Mar. 16, 1990, 247(4948), 1306-1310.

Chiba, "*Helicobacter Pylori*: From The Bench to Bedside", Canadian J Gastro, Oct. 1997, 11(7), 589-596, abstract only.

Chou et al., "Empirical Predictions of Protein Conformation", Annu Rev Biochem, Jul. 1978, 47, 251-276, Abstract.

Creighton, "Protein Structure: A Practical Approach", (no month available) 1989, 184-186.

Creighton, "Proteins: Structures and Molecular Properties", (no month available) 1984, 314-315.

Du et al., "Surface Localized Heat Shock Protein 20 (Hs1V) of Helicobacter", Helicobacter, Aug. 2003, 8(4), 257-267.

Fachinformation, Sanofi Pasteur MSD GmbH, Masern-Impfstoff Merieux, Feb. 2005.

Goetz et al., "Comparison of Selected Analytical Techniques for Protein Sizing, Quantitaion and Molecular Weight Determination", J Biochem Biophys Methods, Sep. 2004, 60(3), 281-293.

Hocking et al., "Isolation of Recombinant Protective *Helicobacter Pylori* Antigens", Infect and Immun, Sep. 1999, 67(9), 4713-4719.

Houghten, "Relative Importance of Position and Individual Amino Acid Residues in Peptide Antigen-Antibody Interactions: Implications in the Mechanism of Antigenic Drift and Antigenic Shift", Vaccines, (no month available) 1986, 86, 21-25.

Kumar, "Amino Acid Variations at a Single Residue in an Autoimmune Peptide Profoundly Affect Its Properties: T-Cell Activation, Major Histocompatibility Complex Binding, and Ability to Block Experimental Allergic Encephalomyelitis", PNAS, Feb. 1990, 87, 1337-1341.

Kyte et al., "A Simple Method for Displaying the Hydropathic Character of a Protein", J. Mol Biol, Jan. 1982, 157(1), 105-132.

Lathe, "Synthetic Oligonucleotide Probes Deduced From Amino Acid Sequence Data. Theoretical and Practical Considerations", J. Mol Biol, May 5, 1985, 183(1), 1-12, Abstract.

Lee, "Animal Models and Vaccine Development", Baillieres Clin Gastroenterology, Sep. 1995, 9(3), 615-632.

Lee, "Development of Epidemiological Method for the *Helicobacter Pylori* by Polymerase Chain Reaction", J. Korean Med Sci, Dec. 1991, 6(4), 338-347.

Medline search conducted in Aug. 2002 for "*Helicobacter pylori* cytotoxin associated immunodominant antigen" Entrez-PubMed, Aug. 8, 2002, 6 pages.

Michetti, "Experimental *Helicobacter Pylori* Infection in Humans: A Multifaceted Challenge", Gut, Jun. 2004, 53, 1220-1221.

Montecucco et al., "Living dangerously: how *Helicobacter pylori* survives in the human stomach", Nat Rev Mol Cell Biol., Jun. 2001, 2(6), 457-466.

Nakayama et al., "*Helicobacter Pylori* VacA Activates the p38/activating Transcription Factor 2-Mediated Signal Pathway in AZ-521 Cells", J. biol chem, Feb. 20, 2004, 279 (8), 7024-7028.

Nosoh et al. (Eds.), "Protein Stability and Stabilization through protein engineering", (no month available) 1991, Chapter 7, 197-217.

Ogura et al., "High prevalence of cytotoxin positive *Helicobacter pylori* in patients unrelated to the presence of peptic ulcers in Japan", Gut, Oct. 1997, 41(4), 463-468.

Orr et al., "cDNA and Deduced Amino Acid Sequence of Drosophila Catalase", Nucleic Acids Research, Oxford University Press, Aug. 25, 1990, 18(12), 3663.

Pauletti, "Application of a Modified Computer Algorithm in Determining Potential Antigenic Determinants Associated with the AIDS Virus Glycoprotein", Anal Biochem, 1985, 151(2), 540-546, Abstract.

Peck et al., "Characterization of Four Members of a Multigene Family Encoding Outer Membrane Proteins of *Helicobacter Pylori* and Their Potential for Vaccination", Microbes and Infection, Marchn2001, 3, 171-179.

Rothel et al., "Urea/DTT solubilization of a recombinant *Taenia ovis* antigen, 45W, expressed as a GST fusion protein results in enhanced protective immune response to the 45W moiety", Vaccine, Apr. 1997, 15(5), 469-472.

Selgrad, "New Strategies for *Helicobacter Pylori* Eradication", Curr Opinion Pharmacol, Jun. 2008, 8, 593-597.

Sipos et al., Cloning and Sequencing of the Genes Coding for the 10- and 60-kDa Heat Shock Proteins From Pseudomonas Aeruginosa and Mapping of a Species-Specific Epitope', Infec Immun, Sep. 1991, 59(9), 3219-3226.

Slomiany et al., "Blockade of p38 Mitogen-Activated Protein Kinase Pathway Inhibits Inducible Nitric Oxide synthase and Gastric Mucosal Inflammatory Reaction to *Helicobacter Pylori* Lipopolysaccharide", Inflammopharmacology, Dec. 2000, 8(4), 371-382.

Spielgelhalder, "Purification of *Helicobacter Pylori* Superoxide Dismutase and Cloning and Sequencing of the Gene", Infect and Immun, Dec. 1993, 61(12), 5315-5325.

Taylor, "Genetics of Campylobacter and Helicobacter", Ann Rev Microbiol, (no month available) 1992, 46, 35-64.

Tombola et al., "The *Helicobacter Pylori* VacA Toxin is a Urea Permease That Promotes Urea Diffusion Across Epithelia", J. Clin Invest, Sep. 2001, 108(6), 929-937.

Vaira et al., "Review article: invasive and non-invasive tests for *Helicobacter pylori* infection", Aliment Pharmacol Ther, Oct. 2000, 14(Suppl.), 13-22.

* cited by examiner

P = Pre-induction with IPTG
1 = isolate 1 post induction
2 = isolate 2 post induction

SEQUENCE LISTING

```
<160> NUMBER OF SEQ ID NOS: 4

<210> SEQ ID NO 1
<211> LENGTH: 46
<212> TYPE: PRT
<213> ORGANISM: Helicobacter pylori

<400> SEQUENCE: 1

Met Lys Thr Phe Glu Ile Leu Lys His Leu Gln Ala Asp Ala Ile Val
1               5                   10                  15

Leu Phe Met Lys Val His Asn Phe His Trp Asn Val Lys Gly Thr Asp
            20                  25                  30

Phe Phe Asn Val His Lys Ala Thr Glu Glu Ile Tyr Glu Glu
            35                  40                  45

<210> SEQ ID NO 2
<211> LENGTH: 64
<212> TYPE: DNA
<213> ORGANISM: Helicobacter pylori

<400> SEQUENCE: 2
gatcgtgtta tttatgaaag tgcataactt ccattggaat gtgaaaggca ccgatttttt     60
caat                                                                  64

<210> SEQ ID NO 3
<211> LENGTH: 25
<212> TYPE: DNA
<213> ORGANISM: Helicobacter pylori

<400> SEQUENCE: 3
gaaggacttc atatgaagac atttg                                           25

<210> SEQ ID NO 4
<211> LENGTH: 27
<212> TYPE: DNA
<213> ORGANISM: Helicobacter pylori

<400> SEQUENCE: 4
cgtgaatgga tcctcatgct gacttct                                         27
```

PROCESS FOR PRODUCTION OF HELICOBACTER PYLORI BACTERIOFERRITIN

CROSS REFERENCE TO RELATED APPLICATIONS

This is a continuation of application Ser. No. 11/326,200, filed Jan. 5, 2006, which is a continuation of application Ser. No. 11/112,735, filed Apr. 22, 2005, which is a continuation of application Ser. No. 10/928,353, filed Aug. 27, 2004, which is a continuation of application Ser. No. 10/699,624, filed Oct. 31, 2003, which is a continuation of application Ser. No. 10/342,431, filed Jan. 13, 2003, which is a continuation of application Ser. No. 10/140,758, filed May 7, 2002, which is a continuation of application Ser. No. 09/101,158, filed Jul. 30, 1998, which is the U.S. National Stage of International Application PCT/IE97/00001, filed Jan. 3, 1997, which claims priority to Irish patent applications IE96004, filed Jan. 4, 1996, and IE960019, filed Jan. 12, 1996, each of which is incorporated herein by reference in its entirety.

FIELD OF THE INVENTION

This invention relates to a 18-19 kDa protein or derivative or fragment thereof obtained from *Helicobacter pylori*, a bacterioferritin defined by sequences in previous patent applications PCT/IE95/00036 and PCT/IE95/00037, a recombinant form of this protein, methods to use this protein as a vaccine to provide immunological protection against if *H. pylori* infection and methods to use this protein in diagnostic assays relating to *H. pylori*.

The contents of previous applications PCT/IE95/00036 and PCT/IE95/00037 are incorporated herein by reference.

BACKGROUND OF THE INVENTION

*Helicobacter pylori* is a widely prevalent organism found on gastric biopsy in approximately 30% of the population less than 40 years old with increasing incidence thereafter. The organism is a causative agent of chronic gastritis in humans (e.g. Marshall & Warren, 1984*; Blaser, 1990*). Epidemiological studies have shown that *H. pylori* is most commonly found in association with gastritis. Serological investigations have demonstrated that evidence of a current or prior infection can be found in 30-50% of a randomly chosen population of blood donors. No direct causal relationship has been conclusively proven for duodenal ulcer disease. However, the organism is found in 95% of patients with duodenal ulcer. Further, eradication of the organism results in rapid ulcer healing (e.g. Rauws & Tytgat, 1990*). These data provide strong evidence that *H. pylori* is a dominant factor in the development of duodenal ulcer. Additional evidence for the pathogenic involvement of *H. pylori* in these conditions has been provided by studies with gnotobiotic piglets (Lambert et al., 1987*) and the fulfilment of Koch's postulates with human volunteers (Marshall et al., 1985*; Morris & Nicholson, 1987*/).

In addition, there is now strong circumstantial evidence implicating *H. pylori* in the pathogenesis of gastric carcinoma (e.g. Jiang et al., 1987*; Lambert et al, 1986*; Crabtree et al., 1992; 1993; Forman et al., 1990, 1991; Nomura et al, 1991; Parsonnet et al., 1991; Correa et al., 1990). Most recently, the Eurogast Study Group, led by Forman (1993), demonstrated a significant relationship between *H. pylori* seropositivity and gastric cancer mortality and incidence. Indeed, there is now a convincing body of literature implicating infection with *H. pylori* in a considerable proportion of upper gastrointestinal morbidity. A number of hypotheses have been suggested for the pathogenic mechanisms of *H. pylori* induced gastroduodenal disease, including the production of cytotoxins and mechanical disruption of the epithelium (e.g. Blaser, 1992*). Interestingly, however, many infected persons remain asymptomatic despite the persistent presence of the pathogen (Taylor & Blaser, 1991*).

Diagnosis of infections with *H. pylori* is based mainly on histology and culture from gastric biopsy specimens or on indirect methods based on urease activity. Various serological assays have been developed for the detection of anti-*H. pylori* antibodies in epidemiological studies in addition to more molecular oriented approaches such as the cloning of *H. pylori* species-specific antigens for use in, for example, PCR-based serological investigations (e.g. Clayton et al., 1989). However, the use of recombinant species-specific antigens has not yet received widespread use and, consequently, the majority of immunosorbent-based assays currently in use employ various subcellular fractions of *H. pylori* as a source of antigen. The fractions of proteins used in these assays are frequently heterogeneous in composition as are their methods of preparation. Interestingly, a number of groups have compared the inter-assay sensitivity and specificity of several commercially available ELISA kits manufactured specifically for serological studies. Not surprisingly, considerable inter-assay variation was observed. Caution, therefore, must be exercised before employing a particular preparation of protein for use in such immunosorbent assays, particularly in view of the significant genetic heterogeneity of different strains of *H. pylori* (e.g. Xia et al., 1994; Owen et al., 1991).

We have studied the prevalence of immuno-reactivity to *H. pylori* in both infected and uninfected individuals and found that un-infected individuals have a high response to *H. pylori* both in their B-cell and T-cell systems. In this approach, we use Western blotting to investigate antigen specificity of systemic responses to *H. pylori* in both healthy and *H. pylori*-infected individuals and show that the incidence of seropositivity in *H. pylori* negative individuals is much greater than has previously been demonstrated. Furthermore, we have demonstrated that antibodies to a 25 kDa protein are detectable in the majority of *H. pylori* negative individuals. These were detected using a technique which we have modified called Enhanced Chemiluminescence. Enhanced Chemiluminescence on Western blot analysis reveals that the majority of uninfected individuals have antibodies which are specific for *H. pylori* and recognize antigens which are not present on other microorganisms. Of these antigens, the most common one recognized is a 18-19 kDa protein which appears to be specific to *H. pylori*. Hence, these data suggest that immunization with the 18-19 kDa protein or sub-unit thereof could have the potential to confer protective immunity on individuals who are either uninfected with the organism or individuals in whom the organism has been cleared by anti-bacterial treatment. We have derived N-terminal and internal amino acid sequences from this protein.

SUMMARY OF THE INVENTION

According to the invention, there is provided a nucleic acid sequence encoding all or part of a *Helicobacter pylori* protein to which immunoreactivity is detected in *H. pylori* negative individuals.

In one embodiment of the invention, the *Helicobacter pylori* protein is an 18-19 kDa protein.

Preferably, the 18-19 kDa protein includes the following the N-terminal amino acid sequence:

```
                                              (SEQ ID NO: 1)
Met-Lys-Thr-Phe-Glu-Ile-Leu-Lys-His-Leu-Gln-Ala-
                  5                      10

Asp-Ala-Ile-Val-Leu-Phe-Met-Lys-Val-His-Asn-Phe-
        15                      20

His-Trp-Asn-Val-Lys-Gly-Thr-Asp-Phe-Phe-Asn-Val-
25                      30                    35

His-Lys-Ala-Thr-Glu-Glu-Ile-Tyr-Glu-Glu.
            40                  45
```

Most preferably, the nucleic acid sequence comprises the following sequence of nucleotides:

```
                                              (SEQ 1ID NO: 2)
5'-GATCGTGTTATTTATGAAAGTGCATAACTTCCATTGGAATGTGAAAG
GCACCGATTTTTTCAAT-3'.
```

The invention also provides a nucleic acid sequence which is complementary to any nucleic acid sequence of the invention.

In one embodiment of the invention, the nucleic acid sequence is genomic DNA, cDNA, synthetic DNA or recombinant DNA.

The invention also provides an oligonucleotide which has a specific binding affinity for a nucleic acid sequence of the invention.

Preferably, the oligonucleotide has one of the following sequences:

```
                                              (SEQ ID NO: 3)
        5'-GAAGGACTTCATATGAAGACATTTG-3';
    or
                                              (SEQ ID NO: 4)
        5'-CGTGAATGGATCCTCATGCTGACTTCT-3'.
```

The invention further provides a vector comprising a recombinant nucleic acid sequence of the invention. Preferably, the vector is an expression vector, most preferably the expression vector pET16b.

The invention also provides a host cell transformed with a vector according to the invention. Preferably, the host cell is one of the following:—

*E. coli* XL1-blue; or

*E. coli* EL21 DE3; or

*E. coli* Novablue DE3.

The invention further provides a process for the production of a recombinant nucleic acid sequence according to the invention comprising culturing a host cell according to the invention and isolating the nucleic acid sequence therefrom.

The invention further provides a recombinant *H. pylori* protein or a fragment thereof whenever expressed from a vector according to the invention.

The invention also provides a process for the production of a recombinant *H. pylori* protein or fragment thereof according to the invention comprising culturing a host cell according to the invention and isolating the protein or protein fragment produced therefrom.

The invention further provides a vaccine including a *H. pylori* protein or a fragment thereof according to the invention.

The vaccine may include a pharmaceutically acceptable carrier.

The vaccine may be combined with a suitable adjuvant such as interleukin 12 or a heat shock protein or both.

The vaccine may include at least one other pharmaceutical product such as an antibiotic and/or an anti-bacterial agent such as bismuth salts. Typically the antibiotic is selected from one or more of metronidazole, amoxycillin, tetracycline, erythromycin, clarithromycin or tinidazole.

The vaccine may be in a form for oral, intranasal, intravenous or intramuscular administration.

The vaccine may include a peptide delivery system.

The vaccine is ideally for the treatment or prophylaxis of *Helicobacter pylori* infection or *Helicobacter pylori* associated disease(s)

The invention also provides a vaccine for the treatment or prophylaxis of *Helicobacter pylori* associated disease comprising an immunogenically effective amount of the *Helicobacter pylori* protein of the invention, an adjuvant such as Interleukin 12, and an antibiotic.

The vaccine may include an antibacterial agent such as bismuth salts.

The invention also includes the use of interleukin 12 in combination with any other recombinant *H. pylori* subunit as an adjuvant therapy.

Therefore, in another, aspect, the invention provides a vaccine against *H. pylori* comprising an immunogenically effective amount of a recombinant *Helicobacter* protein or a subunit, fragment, derivative, precursor or mutant thereof in combination with interleukin 12 as an adjuvant. Preferably, the *Helicobacter* is *Helicobacter pylori*.

In one embodiment of the invention, the vaccine includes an antibiotic and may alternatively or additionally include an antibacterial agent.

The invention also provides a process for the amplification of a nucleic acid sequence according to the invention by a polymerase chain reaction or an equivalent technique.

Preferably, the polymerase chain reaction is effected by using the oligonucleotide pair according to the invention.

The invention also provides a nucleic acid probe comprising a nucleic acid sequence or a fragment thereof according to the invention, or an oligonucleotide according to the invention.

The invention also provides a method for the treatment or prophylaxis of *Helicobacter pylori* associated disease in a host, comprising administering to the host an immunologically effective amount of one or more of the recombinant *Helicobacter* proteins of-the invention.

Preferably, the recombinant *Helicobacter* protein is administered in combination with at least one other pharmaceutical agent.

In a preferred embodiment, the pharmaceutical agent is an antibiotic.

Ideally, the antibiotic is selected from one or more of metronidazole, amoxycillin, tetracycline or erythromycin, clarithromycin or tinidazole.

Typically, the pharmaceutical agent includes an antibacterial agent such as bismuth salts.

In a preferred embodiment of the invention, an adjuvant is administered in combination with the recombinant *Helicobacter* protein. Preferably, the adjuvant is interleukin 12 or a heat shock protein or both.

The invention also provides the use of one or more *Helicobacter* proteins according to the invention for the preparation of a medicament for the treatment or prophylaxis of *Helicobacter pylori* associated disease(s).

The invention further provides monoclonal or polyclonal antibodies or fragments thereof, to the recombinant proteinaceous material of the invention and purified antibodies or serum obtained by immunization of an animal with the vaccine according to the invention.

The invention also provides the use of such serum and antibodies in the treatment or prophylaxis of *Helicobacter* associated disease(s) and in particular *Helicobacter pylori* associated disease(s).

DETAILED DESCRIPTION OF THE INVENTION

Figure 1:
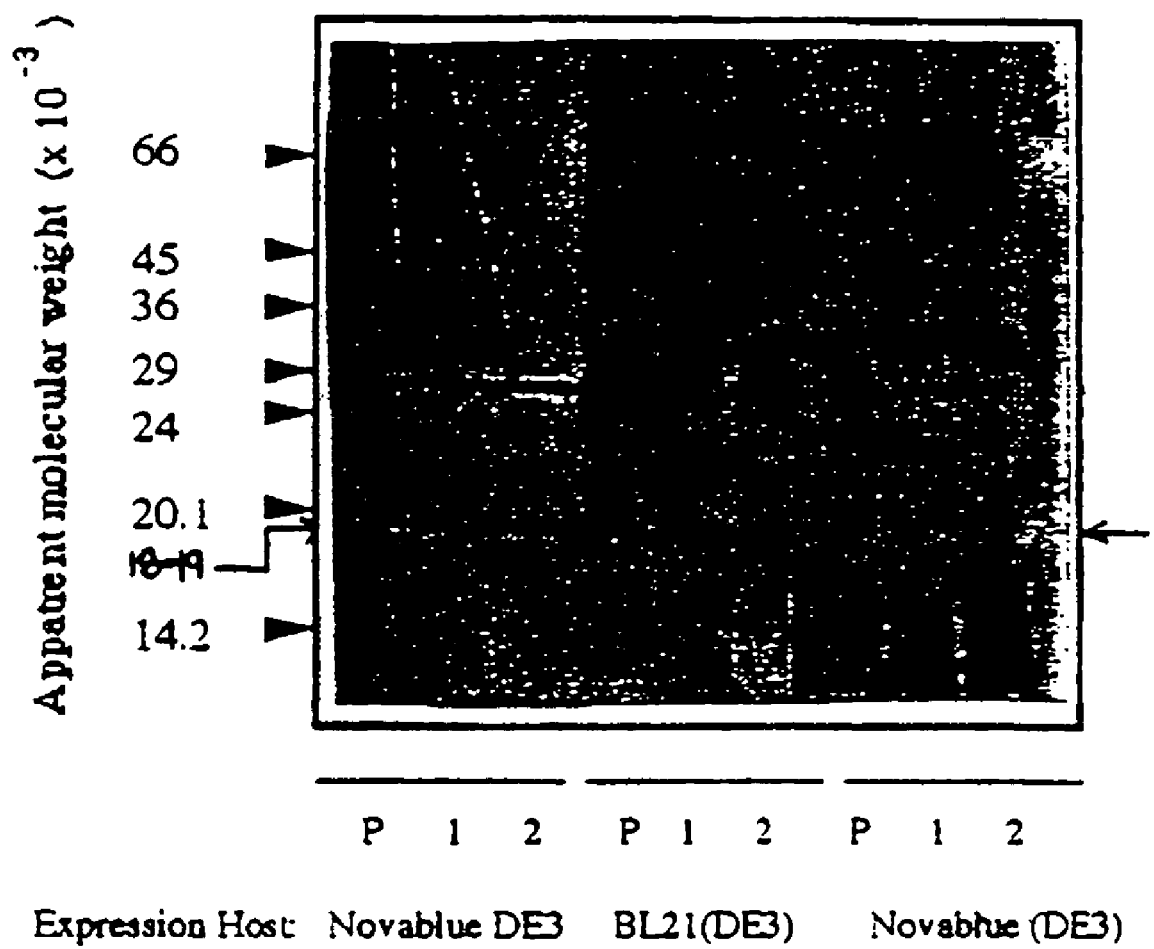
FIG. 1 shows Western blot analysis of the cloned 18 kDa protein. Two transformed *E. coli* expression hosts (BL21 DE3 and Novablue DE3) were subjected to SDS-PAGE (12.5% T) followed by Western blotting analysis. The Western blots were probed with serum obtained from children uninfected with *H. pylori* and developed by enhanced chemiluminescence. Two of the three sera recognized the recombinant 18 kDa protein after induction of expression of the protein with IPTG. In addition, the three sera recognized a number of *E. coli* proteins.

We have generated DNA sequence information identifying the 18-19 kDa protein as a bacterioferritin. We have also generated a recombinant 18 kDa protein and expressed this in *E. coli*. This recombinant protein was found to be recognized immunologically by antisera from individuals positive for antibody to the 18 kDa *helicobacter* bacterioferritin. This recombinant protein will form the basis for a putative vaccine for *H. pylori*. FIG. 1 is a Western Blot analysis of the recombinant 18 kDa protein expressed in *E. coli*.

Methods Employed

Cloning and expression of the *Helicobacter pylori* 18 kDa gene.

Deoxyribonucleic acid (DNA) was extracted from *Helicobacter pylori* as described by Silhavy et al.*(1984).

Oligonucleotides (or "primers") specific for the 5' and 3' termini of the 18 kDa gene were generated. The forward or 5' oligonucleotide (designated HP18CF) was modified to incorporate an Nde 1 restriction endonuclease site. Additional modifications were made to increase the stability of the binding of the oligonucleotide to its target sequence and to prevent intramolecular secondary structure. The sequence of the HP18CF oligonucleotide is (from 5' to 3'):

(SEQ ID NO: 3)
GAAGGACTTCATATGAAGACATTTG

The reverse or 3' oligonucleotide (designated HP18CR) was extensively modified to incorporate a BamH1 restriction endonuclease site and a 5' tail. The 15 3' nucleotides of this oligonucleotide correspond to the *Helicobacter pylori* 18 kDa gene sequence. The sequence of the HP18CR oligonucleotide is (from 5' to 3'):

(SEQ ID NO: 4)
CGTGAATGGATCCTCATGCTGACTTCT

These oligonucleotides were used in a polymerase chain reaction (PCR) to amplify the *Helicobacter pylori* 18 kDA gene sequence. The reaction conditions were as follows: Between 50 and 100 ng of *Helicobacter pylori* DNA was added to 75 pool of each primer, 0.4 mM of each deoxyribonucleotide triphosphate (dNTP), a final concentration of 4 mM $MgSO_4$, 1 fold 'ThermoPol' (New England Biolabs) reaction buffer (composition: 10 mM KCl, 10 mM $(NH_4)_2SO_4$, 20 mM Tris-HCl (pH 8.8 at 25 degrees C.), 2 mM $MgSO_4$, 0.1% Triton X-100), and deionized water was added to bring the reaction volume to 50 ul. The reaction mixture was overlaid with 50 ul paraffin oil and placed in a Perkin-Elmer thermocycle at 90 degrees C. 1 unit vent, DNA polymerase (New England Biolabs) was then added. A 'touch-down' PCR procedure was utilized (Don et al. 1989)*. The cycling conditions were as follows: the DNA was denatured at 94 degrees C. for 2.5 minutes. This was followed by 2 cycles of 94 degrees for 30 seconds (denaturation step), 65 degrees for 50 seconds (annealing step), and 72 degrees C. for 20 seconds (extension step). This was followed by 2 cycles of the same conditions, with the exception that the annealing temperature was dropped 5 to 64 degrees C. After 2 cycles at 64 degrees C., the annealing temperature was reduced to 63 degrees C. for a further 2 cycles, and this pattern was followed until the annealing temperature was reduced to 60 degrees C. for 28 cycles.

The reaction products were purified on a 4% low melting point agarose gel (NuSieve GTG; FMC BioProducts). The DNA fragment was excised from the gel and the agarose was digested using β-Agarase 1 (New England Biolabs) and the DNA recovered following precipitation with isopropanol, according to the manufacturer's supplied protocol.

The purified DNA fragment corresponding to the 18 kDa protein coding gene was then digested with the restriction enzymes Nde 1 and BamN1, (Boehringer Mannheim), each of which occurs only once on the amplified fragment. 10 units of each enzyme was added to approximately 3 ug of DNA in a final concentration of 1× the manufacturer's supplied restriction buffer B in a 40 ul reaction volume. The reaction mix was incubated at 37 degrees C. for 3.5 hours.

The expression vector used was pET16b (Novagen). The 1.6 ug of the vector was digested using Nde1 and BamH 1 under the same conditions as described for the amplified fragment. The resulting 5' phosphate groups were removed using calf intestinal alkaline phosphatase (CIAP: New-England Biolabs) according to the manufacturer's instructions. The enzyme was inactivated by incubating the reaction mixture in the presence of 5 mM EDTA at 65 degrees C. for 1 hour followed by a phenol/chloroform/isoamyl alcohol (25:24:1) extraction, followed by a chloroform/isoamyl alcohol (24:1) extraction.

Both the digested fragment and the digested vector were gel purified on a 3% low melting point agarose gel. (NuSieve GTG; FMC BioProducts), and. the agarose was digested using β-Agarase 1 (New England Biolabs), according to the manufacturer's instructions. The DNA fragments were allowed to remain in the resultant reaction mixture without further purification.

The amplified fragment was then ligated to the vector DNA as follows. Approximately 200 ng of vector was ligated to approximately 100 ng of the insert DNA in 1× ligation reaction buffer and 3 units of T4 DNA ligase (Boehringer Mannheim) in a reaction volume of 30 ul at 20 degrees C. for 16 hours.

The products of this reaction were used to transform competent *E. coli* XL 1-blue cells (Bullock at al. 1987) using a standard $CaCl_2$ transformation procedure (Sambrook, et al., 1989). Transformed XL1-blue cells were selected on LB medium (Sambrook et al., 1989) supplemented with 50 ug per ml ampicillin and grown at 37 degrees C. Suitable colonies were picked and used to inoculate 10 ml LB broth supplemented with 50 ug per ml ampicillin and grown with shaking at 37 degrees C. The plasmids were purified from these cultures using a standard alkaline lysis plasmid preparation procedure (Sambrook, et al., 1989), and an aliquot digested with Nde 1 and KinDZZ7 according to the manufacturers instructions (Boehringer Mannheim) to verify the presence of the insert as compared to a size standard and pET16b without an insert.

Two plasmids shown to have the appropriate insert (designated pET16b-18.1 and pET16b-18.2) were then used to transform the *E. coli* expression hosts BL21 DE3 (Studier and Moffat, 1986) and Novablue DE3 (Novagen) using a standard CaCl$_2$ transformation procedure (Sambrook, et al., 1989●) supplemented with 50 ug per ml ampicillin (Novablue DE3) or 50 ug per ml ampicillin and 34 ug per ml chloramphenicol (SL21 DE3) and grown at 37 degrees C. Transformed cells were selected by plating on solid LB medium. A colony of each host representing each plasmid isolate was picked after 16 hours incubation and used to inoculate 50 ml LB broth supplemented with antibiotics as described above and grown until the optical density at 600 nM was approximately 0.6. The expression of the 18 kDa protein from the expression vector was then induced by the addition of isopropyl b-D-thiogalactopyranoside (IPTG) to 15 a final concentration of 1 mM and incubation was continued for a further 2.5 hours at 37 degrees C. with shaking. The cells were then harvested by centrifugation at 4000×g for 10 minutes and resuspended in 12 ml of 50 mM Tris-HCl (ph 8.0 at 25 degrees C.) followed by a further centrifugation at 4000×g for 10 minutes.

Sequencing the Purified DNA Sequence

The purified DNA fragment corresponding to the 18 kDa protein was sequenced using forward and reverse universal sequencing primers. The DNA was sequenced in the forward and reverse orientations. Sequencing was performed using an ABI automated sequencer and a Genpak PCR based fluorescent dideoxy chain terminator termini sequencing kit.

The sequence of bases between the termini of the internal PCR primers is:

```
                                              (SEQ ID NO: 2)
GATCGTGTTATTTATGAAAGTGCATAACTTCCATTGGAATGTGAAAGGCA
CCGATTTTTTCAAT.
```

Western Blot Analysis of the Cloned Product (18 kDa Protein)

Two transformed *E. coli* expression hosts (BL21 DE3 and Novablue DE3) were subjected to SDS-PAGE (12.5% T) followed by Western blotting analysis. The Western blots were probed with serum obtained from children uninfected with *H. pylori* and developed by enhanced chemiluminescence. As illustrated in FIG. 1, two of the three sera recognised the recombinant 18 kDa protein after induction of expression of the protein with IPTG. In addition, the three sera recognised a number of *E. coli* proteins.

It is understood that the recombinant proteinaceous material of the invention is used as a vaccine against *H. pylori* infection, and in particular as a therapeutic immunogen for eradication of *H. pylori* infection.

The vaccine may include the proteinaceous material according to the invention in combination with other components such as a pharmaceutically acceptable carrier, a suitable adjuvant such as interleukin 12 or a heat shock protein, an antibiotic and/or an antibacterial agent such as bismuth salts. The vaccine may be administered in a number of different ways, namely, orally, intranasally, intravenously or intramuscularly.

The invention is not limited to the embodiments hereinbefore described which may be varied in detail.

REFERENCES

Marshall, B. J. and Warren, J. R. (1984). Unidentified curved bacilli in the stomach of patients with gastritis and peptic ulceration. *Lancet* 1, 1311-1314.

Blaser M. J. (1990). *Helicobacter pylori* and the pathogenesis of gastroduodenal inflammation. *J. Infect. Dis.* 161, 626-633.

Rauws, E. A. J. and Tytgat, G. N. J. (1990). Eradication of *Helicobacter pylori* cures duodenal ulcer: *Lancet* 1, 1233-1235.

Lambert, J. R., Borromeo, M., Pinkard, K. J., Turner, H., Chapman, C. B., and Smith, M. L. (1987). Colonisation of gnotobiotic pigs with *Campylobacter pylori*—an animal model? *J. Infect. Dis.* 155, 1344.

Marshall, B. J. Armstrong, J. A., McGechie, D. B., and Glancy, R. J. (1985). Attempt to fulfil Koch's postulates for pyloric *Campylobacter. Med. J Aust.* 142, 436-439.

Morris, A. and Nicholson, G. (1987). Ingestion of *Campylobacter pylori* causes gastritis and raises fasting gastric pH. *Am. J. Gastroenterol.* 82, 192-199.

Jiang, S. J., Liu, N. Z. Zhang, D. Z., Shi, Y., Xiao, S. D., Zhang, Z. N., and Liu, D. Y. (1987). *Campylobacter*-like organisms in chronic gastritis, peptic ulcer and gastric carcinoma. Scand. J. Gastroenterol. 22, 553-558.

Lambert, J. R., Dunn, K. A, Eaves, F. R., Korman, M. G., and Hansky, J. (1986). *Campylobacter pyloridis* in diseases of the human upper gastrointestinal tract. Gastroenterology 90, 1509.

Crabtree, J. E., Figura, N., Taylor, J. D., Bugnoli, M., Armellini, D., and Tompkins, D. S. (1992). Expression of 120 kDa protein and cytotoxicity in *Helicobacter pylori* J. Clin. Pathol 45, 733-734.

Crabtree, J. E., Wyatt, J. I., Sobala, G. M., Miller, G., Tompkins, D. S., Primrose, J. N., and Morgan, A. G. (1993). Systemic and mucosal humoral responses to *Helicobacter pylori* in gastric cancer. *Gut* 34, 1339-1243.

Forman, D., Sitas, F., and Newell, D. G. (1990) Geographic association of *Helicobacter pylori* antibody prevalence and gastric cancer mortality in rural China. Int. J. Cancer, 46, 608-611.

Forman, D., Newell, D. G., Fullerton, F., Yarnell, J. W. G., Stacey, A. R., Wald, N., and Sitas, F. (1991). Association15 between infection with *Helicobacter pylori* and risk of gastric cancer evidence from. a prospective investigation. *BMJ*302, 1302-1305.

Nomura, A., Stemmermann, G. N., Chyou, P-H., Kato, I., Perez-Perez, G. Z., and Blaser, M. J. (1991). *Helicobacter pylori* infection and gastric carcinoma amongst Japanese Americans in Hawaii, N. Engl. J. Med. 325, 1132-1136.

Parsonnet, J., Friedman, G. D., Vandersteen, D. P., Chang, Y., vogelman, J. K., Orentreich, N., and Sibley, R. K. (1991). *Helicobacter pylori* infection and the risk of gastric carcinoma. *N. Engl. J. Med.* 325, 1127-1131.

Forman, D. (1993). An international association between *Helicobacter pylori* infection and gastric cancer. The EUROGAST Study Group. Lancet 341, 1359-1362.

Blaser, M. J. (1992). Hypothesis on the pathogenesis and natural history of *Helicobacter pylori*-induced inflammation. Gastroenterology 102, 720-727.

Taylor, D. N. and Blaser, M. J. (1991). Epidemiology of *Helicobacter* pylori infection. *Epidemiol Rev.* 13, 42-59.

Bullock, w. 0., Fernandez, J. M. and Short, J. M. 1987. A high efficiency plasmid transforming recA *Escherichia coli* strain with beta-galactosidase selection. *Bio Techniques* 5:376.

Don, R. H., Cox, P. T., Wainwright, B. J., Baker, K. and Mattick, J. S: 1989. 'Touchdown' PCR to circumvent spurious priming during gene amplification. *Nucleic Acids Res.* 19:4008.

Sambrook, J., Fritsch, E. F., and Maniatis, T. 1989. Molecular cloning: a laboratory manual. Second edition. Cold Spring Harbour Laboratory Press.

Silhavy, T. J., Berman, M. L. and Enquist, L. W. 1984. Experiments with gene fusions. Cold Spring Harbour Laboratory Press.

Studier, F. W. and Moffat, B. A. 1986. Use of bacteriophage T7 RNA. polymerase to direct selective high-level expression of cloned genes, *J. Mol. Biol.* 189:113.

The invention claimed is:

1. A process for the production of a recombinant nucleic acid comprising culturing a host cell comprising a vector, said vector comprising the nucleic acid sequence of SEQ ID NO:2 encoding a protein comprising an amino acid sequence of SEQ ID NO:1, and isolating the recombinant nucleic acid therefrom.

2. A process for the production of a recombinant *H. pylori* protein comprising culturing a host cell comprising a vector, said vector comprising a nucleic acid sequence encoding a protein comprising SEQ ID NO:1, wherein said nucleic acid sequence comprises SEQ ID NO:2, and isolating the protein produced therefrom.

3. A process for producing a recombinant *Helicobacter pylori* protein, said process comprising of expressing a *Helicobacter pylori* protein comprising the amino acid sequence of SEQ ID NO:1 from a vector comprising a recombinant nucleic acid sequence comprising SEQ ID NO:2.

4. A process for producing a recombinant *Helicobacter pylori* protein, said process comprising:
   amplifying a nucleic acid encoding a *Helicobacter pylori* protein comprising a molecular weight of 18-19 kDa from *Helicobacter pylori* DNA using a primer comprising SEQ ID NO: 3 and a primer comprising SEQ ID NO: 4;
   inserting said nucleic acid into a vector; and
   expressing said *Helicobacter pylori* protein from said vector.

5. The process of claim 4 wherein said nucleic acid comprises SEQ ID NO: 2.

* * * * *